United States Patent [19]

Fost et al.

[11] Patent Number: 5,215,976
[45] Date of Patent: Jun. 1, 1993

[54] PHOSPHOLIPIDS USEFUL AS SPERMICIDAL AGENTS

[75] Inventors: Dennis L. Fost, Ridgewood; Joseph A. Komor, Ramsey, both of N.J.

[73] Assignee: Mona Industries, Inc., Paterson, N.J.

[21] Appl. No.: 901,205

[22] Filed: Jun. 19, 1992

Related U.S. Application Data

[63] Continuation-in-part of Ser. No. 784,154, Oct. 28, 1991.

[51] Int. Cl.$^5$ ............................................. A61K 31/66
[52] U.S. Cl. .................... 514/114; 514/119; 558/169; 558/170; 558/172
[58] Field of Search ................. 514/114, 119

[56] References Cited

U.S. PATENT DOCUMENTS

| | | | |
|---|---|---|---|
| 3,228,829 | 1/1966 | Wolf et al. | 167/33 |
| 3,304,349 | 2/1967 | Shen | 260/920 |
| 3,830,913 | 8/1974 | Harich | 424/195 |
| 4,202,882 | 5/1980 | Schwartz | 424/76 |
| 4,209,449 | 6/1980 | Mayhew et al. | 260/403 |
| 4,215,064 | 7/1980 | Lindemann et al. | 260/403 |
| 4,233,192 | 11/1980 | Lindemann et al. | 252/545 |
| 4,243,602 | 1/1980 | O'Lenick, Jr. et al. | 260/403 |
| 4,261,911 | 4/1981 | Lindemann et al. | 260/403 |
| 4,283,542 | 8/1981 | O'Lenick, Jr. et al. | 548/112 |
| 4,321,277 | 3/1982 | Saurino | 424/329 |
| 4,323,602 | 4/1982 | Parker | 427/298 |
| 4,336,385 | 6/1982 | Mayhew et al. | 548/112 |
| 4,336,386 | 6/1982 | O'Lenick, Jr. et al. | 548/112 |
| 4,380,637 | 4/1983 | Lindemann et al. | 548/112 |
| 4,503,002 | 3/1985 | Mayhew et al. | 260/945 |
| 4,551,148 | 11/1985 | Riley et al. | 604/890 |
| 4,844,891 | 7/1989 | Rosen et al. | 424/76.4 |
| 4,999,342 | 3/1991 | Ahmad et al. | 514/54 |

OTHER PUBLICATIONS

Mona Industries, Technical Bulletin, No. 905-1a, Apr. 1983.
Mona Industries, Technical Bulletin, No. 905d, Dec. 1989.

*Primary Examiner*—Mary C. Lee
*Assistant Examiner*—Michael G. Ambrose
*Attorney, Agent, or Firm*—Franklyn Schoenberg; Norman E. Lehrer

[57] ABSTRACT

There is provided longlasting contraceptives against human and animal sperm which contain a synthetic phospholipid spermicide of the formula:

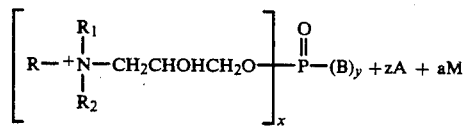

wherein:
x = 1 to 3 or mixtures thereof;
x + y = 3;
z = x;
a = 0 to 2;
B = O$^-$ or OM;
A = Anion;
M is a cation;
R, R$_1$ and R$_2$ are the same or different and are alkyl, substituted alkyl, alkyl aryl or alkenyl groups of up to 16 carbon atoms with the proviso that the total carbon atoms in R + R$_1$ + R$_2$ is between 10 and 24; or

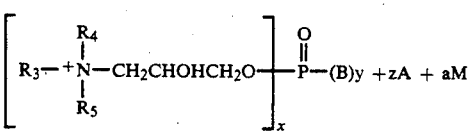

wherein:
x is as hereinabove defined;
x + y = 3;
z = x;
a = 0 to 2;
B = O$^-$ or OM;
A is on Anion;
M is a Cation;
R$_3$ is an amidoamine moiety of the formula:
(Abstract continued on next page.)

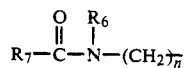

wherein:

$R_7$ is alkyl, alkenyl, alkoxy or hydroxyalkyl of from 5 to 21 carbon atoms each, or aryl or alkaryl of up to 20 carbon atoms;

$R_6$ is hydrogen or alkyl, hydroxyalkyl or alkenyl of up to 6 carbon atoms each or cycloalkyl of up to 6 carbon atoms, polyoxyalkylene of up to 10 carbon atoms;

$R_4$ and $R_5$, which may be the same or different, are selected from alkyl, hydroxyalkyl, carboxyalkyl of up to 6 carbon atoms in each alkyl moiety, and polyoxyalkylene of up to 10 carbon atoms; in addition $R_4$ and $R_5$ taken together with the nitrogen to which they are attached may represent an N-heterocycle; and n is an integer from about 2 to 6.

3 Claims, No Drawings

PHOSPHOLIPIDS USEFUL AS SPERMICIDAL AGENTS

REFERENCE TO RELATED APPLICATION

This application is a continuation-in-part of application Ser. No. 784,154, filed Oct. 28, 1991.

FIELD OF THE INVENTION

The present invention relates to novel antimicrobial compositions and, more particularly, to a class of compounds having specific quaternized amine compounds linked to specific phosphate esters which exhibit antimicrobial activity and also spermicidal activity referred to hereinafter as "antimicrobial/ spermicidal phospholipids". The phospholipids of the invention are well tolerated by human tissue making them suitable for use in the preparation of therapeutic, personal care and the like products which are useful as a contraceptive and for the immobilization and/or killing of human and animal sperm.

BACKGROUND OF THE INVENTION

Phosphate ester and quaternary amine compounds are well known and have been widely used for many years for a variety of applications including those requiring surfactant properties. Known phosphate esters do not generally exhibit any antimicrobial characteristics, and while quaternary amine compounds are known in general to exhibit antimicrobial activity, such compounds are extremely irritating and thus have limited usefulness in personal care and cosmetic products. More recently, various betaine-type derivatives having, in general, quaternized alkyl amine groups and at least one phosphorus-containing anion in the molecule referred to hereinafter as "synthetic phospholipids", have been disclosed and suggested as, for example, in U.S. Pat. Nos. 4,215,064, 4,233,192 and 4,380,637 to Lindemann et al., U.S. Pat. Nos. 4,209,449, 4,336,385 and 4,503,002 to Mayhew et al., and U.S. Pat. Nos. 4,243,602, 4,283,542 and 4,336,386 to O'Lenick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, household cleaning and the like products, such products also require the incorporation of antimicrobial preservatives to inhibit microbial spoilage and increase shelf life, and there is no suggestion that any of these compounds exhibits spermicidal activity.

SUMMARY OF THE INVENTION

In accordance with the present invention there has now been discovered novel phospholipid agents which surprisingly exhibit both excellent broad spectrum antibacterial and antifungal activity suitable for use as preservative and/or disinfectant agents in a variety of personal care compositions, household cleaning formulations; and the like. These agents have also been found to possess potent spermicidal activity making them particularly useful as a contraceptive, and for immobilizing and/or killing human and animal sperm for extended periods of time. The novel antimicrobial agents of the invention which also exhibit spermicidal properties comprise particular synthetic phospholipid compounds that may be represented by the following general formula:

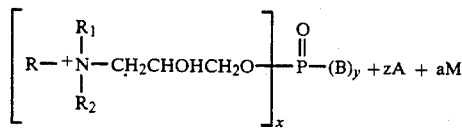

wherein:
x = 1 to 3 or mixtures thereof;
x + y = 3;
z = x;
a = 0 to 2;
B = O$^-$ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in R+$R_1$+$R_2$ is between 10 and 24.

It has been discovered that the particular synthetic antimicrobial phospholipids of the invention not only surprisingly and unexpectedly exhibit both broad spectrum bactericidal and fungicidal activity suitable for use as preservative and/or disinfectant agents in personal care and household products, but such phospholipid compositions surprisingly also exhibit potent spermicidal activity making them useful as a contraceptive and in topical and therapeutical compositions for killing and/or immobilization of sperm. Even small amounts of the phospholipid compositions of the invention exhibit effective antimicrobial and spermicidal activity and the antimicrobial phospholipid compounds of the invention are substantive to human and animal tissue as well as many known substrate materials such as used in contraceptives and the like. Moreover, such agents are extremely well tolerated by human tissue, i.e., they exhibit exceptionally low ocular and skin irritation and oral toxicity, and can be used in product formulations containing nonionic, anionic, amphoteric and/or cationic components without significant inhibition or reduction of the required antimicrobial and/or spermicidal activity. Thus, such agents may be formulated into a wide range of end products among which are germicidal cleaning compositions for hospitals and the like. The antimicrobial agents of the invention may also be used in combination with other known antimicrobial agents, when desired for particular applications, to enhance the antimicrobial effectiveness thereof.

In another aspect of the invention, there is provided a method of inhibiting the growth of microorganisms in personal care, household cleaning and the like products which comprises incorporating in a personal care or household cleaning formulation an antimicrobially effective amount of an antimicrobial phospholipid compound of the general formula:

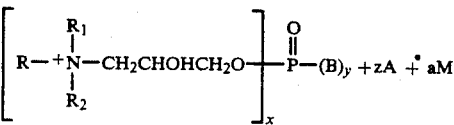

wherein:
x = 1 to 3 or mixtures thereof;
x + y = 3;

z = x;
a = 0 to 2;
B = O⁻ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

In a still further aspect of the present invention, there is provided a personal care composition or a household cleaning composition which comprises a surface active agent and an antimicrobial effective amount of an antimicrobial phospholipid compound component of the general formula:

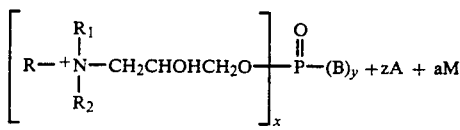

wherein:
x = 1 to 3 or mixtures thereof;
x + y = 3;
z = x;
a = 0 to 2;
B = O⁻ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R^1+R_2$ is between 10 and 24.

In yet another aspect of the invention there are provided compositions for topical or therapeutic use in the killing and/or immobilizing of human and animal sperm including contraceptive protection which comprises a carrier and a spermicidally effective amount of an antimicrobial/spermicidal phospholipid agent of the general formula:

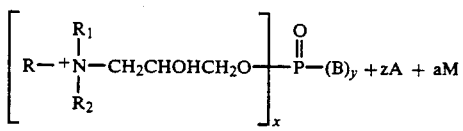

wherein:
x = 1 to 3 or mixtures thereof;
x + y = 3;
z = x;
a = 0 to 2;
B = O⁻ or OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24;
or a spermicidal agent of the general formula:

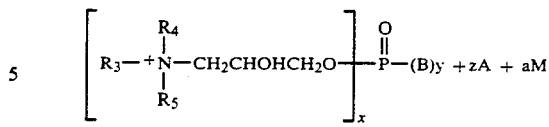

wherein:
x is as hereinabove defined;
x + y = 3;
z = x;
a = 0 to 2;
B = O⁻ or OM;
A is on Anion;
M is a Cation;
$R_3$ is an amidoamine moiety of the formula:

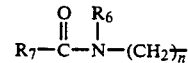

wherein:
$R_7$ is alkyl, alkenyl, alkoxy or hydroxyalkyl of from 5 to 21 carbon atoms each, or aryl or alkaryl of up to 20 carbon atoms;
$R_6$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkylene of up to 10 carbon atoms;
$R_4$ and $R_5$, which may be the same or different, are selected from alkyl, hydroxyalkyl, carboxyalkyl of up to 6 carbon atoms in each alkyl moiety, and polyoxyalkylene of up to 10 carbon atoms; in addition $R_4$ and $R_5$ taken together with the nitrogen to which they are attached may represent an N-heterocycle; and
n is an integer from 2 to 6.

As used herein the phrases "antimicrobial" and "inhibiting microbial growth" describes the killing of, as well as the inhibition or control of the growth of bacteria (gram positive and gram negative), fungi, yeasts and molds.

As used herein the phrase "spermicidal" describes sperm immobilization as well as the killing of human and animal sperm.

DETAILED DESCRIPTION OF THE INVENTION

The present invention is directed to novel phospholipid agents which surprisingly and unexpectedly exhibit excellent broad spectrum bactericidal and fungicidal activity and effectiveness, effectively inhibit the growth of a variety of bacteria, yeasts, and molds and effectively immobilize and/or kill human and animal sperm. Moreover, such active agents may be used in combination with or in the presence of anionic, nonionic, amphoteric and/or cationic surfactants without inhibition of the antimicrobial efficacy thereof and are virtually non-irritating to the skin and eyes; thus, such antimicrobial agents may be used in diverse formulations and applications.

The novel antimicrobial/spermicidal agents of the present invention comprise a class of synthetic phospholipid compounds which may be represented by the following general formula:

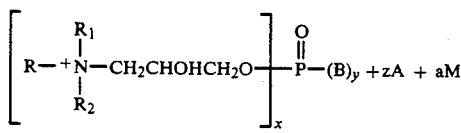

wherein:
x = 1 to 3 or mixtures thereof;
x + y = 3;
z = x;
a = 0 to 2;
B = O⁻, OM;
A = Anion;
M is a cation;
R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

The antimicrobial/spermicidal phospholipid compounds described which, as indicated, exhibit broad spectrum antimicrobial as well as spermicidal activity while being substantially non-irritating to humans can be prepared by reaction of tertiary amines and phosphate esters corresponding to the amine and phosphate ester moieties in the above formula. Such compounds can be prepared by reacting the corresponding tertiary amine and phosphate ester reactants in the molar ratio of 1:1 to 3:1, and preferably from about 2.0:1 to 2.5:1 of amine to phosphate ester, for the time necessary for the amine to be completely reacted.

Tertiary amines suitable for use in accordance with the practice of the invention can be represented by the general formula:

wherein R, $R_1$ and $R_2$ are the same or different and are alkyl, substituted alkyl, alkyl aryl, or alkenyl groups of up to 16 carbon atoms with the proviso that the total carbon atoms in $R+R_1+R_2$ is between 10 and 24.

Exemplary tertiary amines include:
tributylamine
(di(hydroxyethyl)hexyl)-amine
bis(2-hydroxyethyl)cocoamine
N,N-dimethyl-dodecylamine
N,N-dimethyl-tetradecylamine
N,N-dimethyl-hexadecylamine
N,N-dimethyl-cocoamine
N,N-dimethyl-cetylamine
dimethyl ($C_8$–$C_{16}$) alkyl amine The phosphate ester reactants suitable for use in accordance with the practice of the invention can be represented by the general formula:

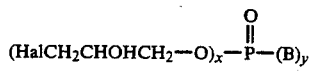

wherein:
x = 1 to 3 or mixtures thereof;
x + y = 3;
B = O⁻ or OM;
Hal = halogen.

The phosphate ester intermediate may be prepared by known procedures wherein phosphoric acid and various phosphate salts, and preferably monosodium phosphate, are reacted in an aqueous medium with epichlorohydrin, generally in the molar ratio of about 1:1 to 1:3, until the reaction is complete.

As noted, the instant invention is based upon the discovery that the phospholipid compounds of the invention described above are effective in controlling the growth of bacteria, yeasts and molds in diverse formulations and applications such as cosmetic, toiletries, personal care, household and related products and materials. The phospholipid agents of the invention are not only effective antimicrobials for the destruction or control of fungi and bacteria that cause degradation and deterioration of diverse personal care and household product formulations, but also by their activity against the organisms that can reside and accumulate on various surfaces, can provide utility in sanitizing, disinfecting and bacteriostatic applications.

The antimicrobial activity of the compounds described above has been confirmed using standard laboratory techniques, including the Minimum Inhibitory Concentration (MIC) technique. They have been found effective, for example, in inhibiting bacteria including *S. aureus, E. coli, P. aeruginosa* and *S. choleraesuis*. They have also been found effective against yeast and mold including *C. albicans* and *A. niger*. In these tests it has been determined that the presence of anionic, nonionic, amphoteric and/or cationic materials did not inhibit the antimicrobial efficacy nor did a variety of inactivators commonly encountered in personal care and household applications. The broad spectrum preservative characteristics of the antimicrobial phospholipids of the invention in typical cosmetic formulations have also been established and confirmed.

Specifically, molds and yeasts which may be inhibited include *Aspergillus niger, Candida albicans* plus various species of Penicillium, Tricholphyton, Alternaria, Gliocladium, Paecilomyces, Mucor, Fusarium, Geotrichum, Cladosporium and Trichoderma. Examples of the bacteria include *Salmonella choleraesuis, Serratia marcescens, Klebsiella pneumoniae, Enterobacter aerogenes, Aerobacter aerogenes, Proteus vulgaris, Streptococcus faecalis, Pseudomonas aeruginosa, Escherichia coli, Staphylococcus aureus, Staphylococcus epidermidis, M. luteus, P. mirabilis, P. cepacia, P. stutzeri* and *A. hydrophilia*.

Another aspect of the present invention is the discovery that the antimicrobial phospholipid compounds surprisingly and unexpectedly exhibit significant spermicidal and antiviral activity which further enhances the utility of the compounds of the invention for a diversity of applications.

The spermicidal activity of the phospholipid compounds described above has been confirmed using test methodology based on the International Planned Parenthood Federation (IPPF) spermicidal assay as set forth in 21CFR, Part 351, Volume 45, No. 241. Substantivity to human skin as well as known latex and fabric substrate materials treated with aqueous solutions of the phospholipid compounds that were submitted to repeat washing microbiological test protocol have shown such compounds to possess residual antimicrobial activity for extended periods of time.

The phospholipid compounds described above have activity against bacteria, yeasts, molds as well as human and animal sperm when employed at appropriate levels of concentration and may be used to inhibit growth or effectively destroy these organisms. It should be obvious that the required effective concentration or amount will vary with particular organisms and also on a number of other factors in particular applications. In general, however, effective antimicrobial response is obtained when the active agent is employed in concentrations ranging between five and 10,000 ppm (parts per million) and preferably between about 50 and 1000 ppm. Generally, the concentration of the agent required for bactericidal activity will be lower than the concentration required for fungicidal activity and the concentration of the agent required for spermicidal activity will generally be the same or greater than required for fungicidal activity.

For other applications, amounts of from 0.04% to about 5% or higher, preferably 0.07% to about 3.0%, by weight of the active agent of the present invention is incorporated into a composition or sprayed onto or otherwise applied to a substrate to be treated in order to prevent growth of bacteria, yeasts, molds as well as killing human and animal sperm. It will also be understood that the antimicrobial agents of the invention may be used in combination with other antimicrobial and/or spermicidal materials.

The compatibility of the phospholipid compounds of the invention with human tissue, i.e., dermal and eye tissue has also been tested. In these tests, 48 hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

While the antimicrobial/spermicidal phospholipid compounds hereinabove described exhibit broad spectrum antimicrobial as well as potent spermicidal activity, certain other phospholipid compounds which do not possess broad spectrum antimicrobial activity surprisingly have also been found to possess potent spermicidal activity along with suitable compatibility with anionic, nonionic, amphoteric and/or cationic materials without inhibition of their spermicidal efficacy or sensitivity with human tissue.

Phospholipid compounds which are also suitable for use as spermicidal agents have the general formula:

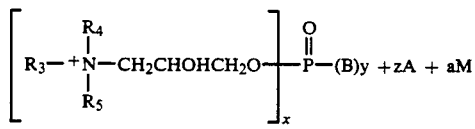

wherein:
x is as hereinabove defined;
x+y=3;
z=x;
a=0 to 2;
B=O$^-$ or OM;
A is on Anion;
M is a Cation;
R$_3$ is an amidoamine moiety of the formula.

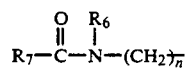

wherein:

R$_7$ is alkyl, alkenyl, alkoxy or hydroxyalkyl of from 5 to 21 carbon atoms each, or aryl or alkaryl of up to 20 carbon atoms;

R$_6$ is hydrogen or alkyl, hydroxyalkyl or alkenyl of up to 6 carbon atoms each or cycloalkyl of up to 6 carbon atoms, preferably of from 2 to 5 carbon atoms or polyoxyalkylene of up to 10 carbon atoms;

R$_4$ and R$_5$, which may be the same or different, are selected from alkyl, hydroxyalkyl, carboxyalkyl of up to 6 carbon atoms in each alkyl moiety, and polyoxyalkylene of up to 10 carbon atoms, in addition R$_4$ and R$_5$ taken together with the nitrogen to which they are attached may represent an N-heterocycle; and n is an integer from 2 to 6.

The antimicrobial phospholipid compounds of the invention may be incorporated in diverse personal care and household product formulations as, for example, a preservative therefore and/or as a disinfectant agent, and the incorporation of the compounds of the invention into such products can be done in accordance with standard practices. The active ingredients described can be diluted or otherwise mixed with solvents, dispersants, wetting agents, carriers and the like for topical, therapeutic use as a spermicide in any desired application formulation such as liquids, jellies, creams, tablets, suppositories, foams etc. In connection with suitable modes of application for spermicidal results, the phospholipid agents can be mixed with one or more pharmaceutically acceptable solid inert carriers.

The invention will now be further illustrated by reference to certain specific examples which are provided herein for purposes of illustration only and are not intended to limit the scope therein.

EXAMPLE 1

925.6 grams of soft water are charged to a reaction vessel and heat is applied to 50° C. 554.4 grams of dimethyl cocoamine (C$_{12}$-66%; C$_{14}$-26%; C$_{16}$-8%) are charged into the reaction vessel under good agitation and heat is applied to 90° C. An aqueous solution of 938.8 grams of 40% active 2-propanol, 1-chlorophosphate (3:1) are charged into the reaction vessel in four equal increments over 1.5 hours using good agitation while maintaining the temperature at 90°-95° C. Heating is continued at 90°-95° C. until the pH (10%) is 6.5 or less and the percentage of free tertiary amine is 0.5% maximum; approximately six to nine hours. The reaction mixture is then cooled to 80° C., 55.2 grams of 50% NaOH are charged into the reaction vessel and the reaction mixture is heated back to 90° C. Heating at 90° C. is continued until the percentage of NaCl is 6.9±0.2%, approximately one hour. The reaction mixture is then cooled to 50° C. and the pH (10%) is adjusted to 7.0±0.5 with citric acid (approximately 9.7 grams). 22.1 grams of H$_2$O$_2$ (35%) are charged to the reaction vessel with good agitation and heat is applied to 90° C. and maintained for one hour. The reaction mixture is then cooled to 50° C. and discharged. The product is a clear liquid having <0.5% free amine, a pH (10%) of 7.0±0.5 and a specific gravity @25° C. of 1.05.

EXAMPLE 2

682.4 grams of propylene glycol and 453.0 grams of water are charged to a reaction vessel and heat is applied to 50° C. 655.2 grams of dimethyl cetylamine are charged into the reaction vessel with good agitation and heat is applied to 90° C. An aqueous solution of 938.8 grams of 40% active 2-propanol, 1 chlorophosphate (3:1) are divided into four equal increments and charged into the reaction vessel over 1.5 hours while maintaining the temperature at 90°–95° C. Heating is continued at 90°–95° C. until the pH (10%) is 6.5 or less and the free tertiary amine is <0.5%, approximately six to nine hours. The reaction mixture is then cooled to 80° C. and 47.3 grams of 50% NaOH is added with good agitation. Heat is applied to 90° C. and maintained until the percentage of NaCl is 6.1±0.2%, approximately one hour. The reaction mixture is then cooled to 50° C. and the pH (10%) is adjusted to 7.0±0.5 with citric acid, approximately 4.7 grams being added. 25 grams of 35% $H_2O_2$ are charged into the reaction vessel, heat is applied to 90° C. and maintained for one hour. The reaction mixture is then cooled to 50° C. and discharged.

The product is a clear liquid having a specific gravity @25° C. of 1.05, a pH (10%) of 7.0±0.5 and Free amine of <0.5%.

EXAMPLE 3

The products of Example 1 and Example 2 are screened for antimicrobial activity using a modified Minimum Inhibitory Concentration (MIC) testing protocol. The initial screening is conducted using the following test organisms:
S. aureus ATCC #6538
C. albicans ATCC #10259
A. niger ATCC #6275
Penicillium variable ATCC #XXXX The growth media used are Brain Heart Infusion Broth for bacteria and Sabouroud Broth for yeast and mold.

A series of ten sequential two-fold dilutions of the test material is made in an appropriate growth promoting culture medium for each organism to be tested. A standard number of microorganisms are inoculated into each of the prepared dilutions containing the medium plus the test material. Inoculated tubes are incubated at appropriate temperature for 72 hours.

Visual readings are taken after 24, 48 and 72 hours. The 72-hour incubated tubes are subcultured on agar media to verify inhibition of growth. Data are recorded as positive or negative for growth at each of the dilutions of the test material under evaluation. The minimum lethal concentration is defined as the smallest concentration of antimicrobial agent that, on subculture, either fails to show growth or results in a 99.9% decrease in the initial concentration of inoculum.

Comparative MIC data of the initial screening test are reported in Table I.

TABLE I

| Test Organism | Example I Sample | Example II Sample |
|---|---|---|
| S. aureus | 20 ppm | 60 ppm |
| C. albicans | 20 ppm | 80 ppm |
| A. niger | 10 ppm | 30 ppm |
| P. variable | 10 ppm | 80 ppm |

An additional test panel is conducted to evaluate the products of Example 1 and Example 2. The further tests are conducted with Pseudomonas aeruoinosa ATCC #15442, E. coli ATCC #8739 and Salmonella choleraesuis ATCC #10708. The MIC test protocol described above is used in conducting the additional test.

Comparative MIC data of the additional screening test are reported in Table II.

TABLE II

| Test Organism | Example 1 | Example 2 |
|---|---|---|
| P. aerugenosa | 80 ppm | 80 ppm |
| E. coli | 20 ppm | 160 ppm |
| S. choleraesuis | 20 ppm | 80 ppm |

As can be seen, both the Example 1 and Example 2 products exhibit significant antimicrobial properties.

EXAMPLE 4

A series of typical personal care products are prepared by standard practices using the following proportion of ingredients:

| Product A | Shampoo | |
|---|---|---|
| | Sodium Lauryl Sulfate | 15.0% by weight |
| | Water | 85.0% |
| | Antimicrobial Phospholipid (Example 1) | variable |

Compositions are prepared with the following proportions of the product of Example 1.

| Test Sample | Example 1 Product |
|---|---|
| A-1 | 0.00% by weight |
| A-2 | 0.25% by weight |
| A-3 | 0.50% by weight |
| A-4 | 1.00% by weight |

| Product B | Make-Up Foundation | |
|---|---|---|
| | (a) Steareth - 20 | 1.5% by weight |
| | Pigment | 15.0% by weight |
| | 0.5% Kelzan AR/1% NaCl | 76.0% by weight |
| | (b) Steareth - 2 | 2.5% by weight |
| | Isopropyl Myristate | 2.0% by weight |
| | Hexyl Laurate | 2.0% by weight |
| | Dow Fluid 200/100 cs | 1.0% by weight |
| | Antimicrobial Phospholipid | variable |
| | Pigment: White | 13.50% by weight |
| | Red | 0.15% by weight |
| | Brown | 1.20% by weight |
| | Yellow | 0.15% by weight |

Compositions are prepared with the following proportions of the product of Example 1.

| Test Sample | Example 1 Product |
|---|---|
| B-1 | 0.00% by weight |
| B-2 | 0.25% by weight |
| B-3 | 0.50% by weight |
| B-4 | 1.0% by weight |

| Product C | Lotion | |
|---|---|---|
| | (a) Steareth - 20 | 2.0% by weight |
| | Water | 87.5% by weight |
| | Product of Example 1 | variable |
| | (b) Steareth - 2 | 3.0% by weight |
| | Isopropyl Myristate | 5.0% by weight |
| | Cetearyl Alcohol | 2.5% by weight |

Compositions are prepared with the following proportions of the product of Example 1.

| Test Sample | Example 1 Product | |
|---|---|---|
| C-1 | Product of Example 1 | 0.0% by weight |
| C-2 | Product of Example 1 | 0.1% by weight |
| C-3 | Product of Example 1 | 0.5% by weight |

EXAMPLE 5

The personal care products of Example 4 are subject to Preservative Challenge Tests as follows:

Aliquots of each test preparation are inoculated with separate representative mixed cultures of bacteria and fungi. Plate counts to determine survivors are performed at 0 time and after 3, 7, 14, 21 and 28 days of incubation. Bacterial samples showing a less than 10 recovery at 14 days are re-inoculated at 21 days. Results are presented as surviving organisms present at each time interval per gram of product tested.

PRODUCT A
INOCULUM (a) Mixed bacteria: *Pseud. aeruginosa* (ATCC 15442); *E. coli* (ATCC 8739 or 11229); *S. aureus* (ATCC 6536).
(b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL |
|---|---|---|---|---|
| A-1 | 0 | 2,100,000 | 740,000 | <10 |
|  | 3 | 17,500 | 4,750 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| A-2 | 0 | 2,100,000 | 740,000 | <10 |
|  | 3 | 24,200 | 1,900 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-3 | 0 | 2,100,000 | 740,000 | <10 |
|  | 3 | 16,900 | 9,700 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-4 | 0 | 2,100,000 | 740,000 | <10 |
|  | 3 | 23,700 | 1,620 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE: Control is an uninoculated sample for background count. Bacterial and Fungal Counts are as organisms recovered per gram of sample. Test Day is the number of days after inoculation of the test sample.

As can be seen, the antimicrobial product of Example #1 is highly effective against both bacterial and fungal challenges at a concentration of 0.25%. Moreover, the antimicrobial product of Example #1 is not adversely affected by anionics such as sodium lauryl sulfate.

PRODUCT B
INOCULUM (a) Mixed bacteria: *Pseud. aeruginosa* (ATCC 15442); *E. coli* (ATCC 8739 or 11229); *S. aureus* (ATCC 6536).
(b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL |
|---|---|---|---|---|
| B-1 | 0 | 2,100,000 | 740,000 | <10 |
|  | 3 | 2,100,000 | 740,000 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| B-2 | 0 | 1,980,000 | 750,000 | <10 |
|  | 3 | 57,000 | 4,200 | <10 |
|  | 7 | <10 | 120 | <10 |
|  | 14 | <10 | 1,420 | <10 |
|  | 21* | <10 | 5,300 | <10 |
|  | 28 | <10 | 7,400 | <10 |
| B-3 | 0 | 2,100,000 | 740,000 | <10 |
|  | 3 | 12,000 | 3,400 | <10 |
|  | 7 | <10 | <10 | <10 |
|  | 14 | <10 | <10 | <10 |
|  | 21* | <10 | <10 | <10 |
|  | 28 | <10 | <10 | <10 |
| B-4 | 0 | 2,100,000 | 700,000 | <10 |
|  | 3 | 3,000 | <10 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE: Control is an uninoculated sample for background count. Bacterial and Fungal Counts are as organisms recovered per gram of sample. Test Day is the number of days after inoculation of the test sample.

As can be seen, the antimicrobial product of Example #1 is highly effective against both bacterial and fungal challenges at a concentration of 0.50%. At 0.25%, the product of Example #1 is effective against the bacterial inoculum but failed to completely eradicate the fungi after initial reductions were noted.

PRODUCT C
INOCULUM (a) Mixed bacteria: *Pseud. aeruginosa* (ATCC 15442); *E. coli* (ATCC 8739 or 11229); *S. aureus* (ATCC 6536).
(b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL (Uninoculated) |
|---|---|---|---|---|
| C-1 | 0 | 2,100,000 | 310,000 | 610 |
|  | 3 | 2,700,000 | 350,000 | 1,220 |
|  | 7 | TNTC* | TNTC | TNTC |
|  | 14 | TNTC | TNTC | TNTC |
|  | 21 | TNTC | TNTC | TNTC |
|  | 28 | TNTC | TNTC | TNTC |
| C-2 | 0 | 2,400,000 | 250,000 | <10 |
|  | 3 | <10 | 6,340 | <10 |
|  | 7 | <10 | 5,100 | <10 |
|  | 14 | <10 | 1,260 | <10 |
|  | 21* | <10 | 2,140 | <10 |
|  | 28 | <10 | 2,970 | <10 |
| C-3 | 0 | 1,900,000 | 290,000 | <10 |
|  | 3 | <10 | 2,170 | <10 |
|  | 7 | <10 | <10 | <10 |
|  | 14 | <10 | <10 | <10 |
|  | 21* | <10 | <10 | <10 |
|  | 28 | <10 | <10 | <10 |

*TNTC - Too Numerous to Count
*21-day Re-inoculation
NOTE: Control is an uninoculated sample for background count. Bacterial and Fungal Counts are as organisms recovered per gram of sample. Test Day is the number of days after inoculation of the test sample.

As can be seen, Test sample C-3 (0.5% Product of Example #1) is found to effectively eliminate both bacterial and fungal challenges within seven days of inoculation. The product of Example #1 at 0.5% is capable of functioning effectively as a preservative as measured by the above test parameters.

The antimicrobial test results clearly show the effectiveness of these products in preserving these systems. Noteworthy is the fact that product of Example #1 is not affected by anionics such as sodium lauryl sulfate.

EXAMPLE 6

Using in vitro test methodology based on the International Planned Parenthood Federation (IPPF) Agreed Test for Total Spermicidal Power as set forth in 21 CFR, Part 351, Volume 45, No. 2/541, Dec. 12, 1980, evidence of spermicidal activity against human sperm is evaluated for contraceptive efficacy.

The product of Example 1 is screened for spermicidal activity by evaluation of 1.0%, 3.0% and 5.0% aqueous solutions thereof.

The 3.0% and 5.0% solutions of the product of Example 1 meet the requirements of the IPPF Agreed test by inactivation of human sperm after ten (10) second contact time.

EXAMPLE 7

The skin substantivity of the product of Example 1 is evaluated by a multiple wash test protocol.

Individual fingers of selected panelists are washed twice, dried and exposed to the test material. Once exposed, finger imprints are made on agar plates seeded with *Staphylococcus epidermidis* after which the individual fingers are again washed and dried. A series of four (4) washings and imprints are made, including the initial exposure and imprint. The degree of residual activity or skin substantivity is determined by clarity of inhibition surrounding the imprints on the agar plates (seeded with Staphylococcus epidermidis). A grading system is used to record the data as follows:

```
0:  no activity;
1+: slight activity;
2+: moderate activity;
3+: good;
4+: excellent.
```

Skin substantivity data are reported in Table III.

TABLE III

| Panelist | 1 | 2 | 3 | 4 | 5 | Avg. |
|---|---|---|---|---|---|---|
| 1.0% Solution Conc. | | | | | | |
| Treated | 4+ | 2+ | 2+ | 3+ | 2+ | 2.6 |
| Wash 1 | 3+ | 2+ | 2+ | 2+ | 1+ | 2.0 |
| Wash 2 | 2+ | 0 | 1+ | 0 | 0 | 0.6 |
| Wash 3 | 1+ | 0 | 0 | 0 | 0 | 0.2 |
| Untreated | NT | 0 | 0 | 0 | 0 | 0.0 |
| 3.0% Solution Conc. | | | | | | |
| Treated | 4+ | 4+ | 4+ | 4+ | 4+ | 4.0 |
| Wash 1 | 3+ | 3+ | 3+ | 3+ | 3+ | 3.0 |
| Wash 2 | 3+ | 1+ | 1+ | 2+ | 1+ | 1.6 |
| Wash 3 | 1.5+ | 0 | 0 | 1+ | 0 | 0.5 |
| Untreated | NT | 0 | 0 | 0 | 0 | 0.0 |
| 5.0% Solution Conc. | | | | | | |
| Treated | NT | 4+ | 4+ | 4+ | 4+ | 4.0 |
| Wash 1 | NT | 3+ | 4+ | 3+ | 3+ | 3.1 |
| Wash 2 | NT | 3+ | 3+ | 1+ | 2+ | 2.3 |
| Wash 3 | NT | 1+ | 2+ | 0 | 1+ | 1.0 |
| Untreated | NT | 0 | 0 | 0 | 0 | 0.0 |

NT - not tested

EXAMPLE 8

The substantivity of the product of Example 1 to lambskin and latex-type condoms is evaluated by a multiple wash test protocol of the type described in Example 7.

In this study, two (2) cm. squares of prewashed and dried condom materials are exposed to the test materials by dipping into a test solution and blotting to remove excess moisture. Once exposed, the squares are laid on seeded agar plates (seeded with *Staphylococcus epidermidis*). A series of four (4) washings including the initial exposure are carried out. The degree of residual activity or condom substantivity is determined by the clarity of the zone of inhibition surrounding the treated and washed squares on the seeded agar plates as compared to the untreated controls. The grading system described in Example 7 is used to record the data obtained.

Lambskin condom substantivity data is reported in Table IV and latex condom substantivity data is reported in Table V.

TABLE IV

| SWATCH | 1 | 2 | Avg. |
|---|---|---|---|
| 1.0% Solution | | | |
| Treated | 4+ | 4+ | 4.0 |
| Wash 1 | 4+ | 4+ | 4.0 |
| Wash 2 | 4+ | 4+ | 4.0 |
| Wash 3 | 4+ | 4+ | 4.0 |
| Untreated | 0 | 0 | |
| Rating Score | | | 16.0 |
| 3.0% Solution | | | |
| Treated | 4+ | 4+ | 4.0 |
| Wash 1 | 4+ | 4+ | 4.0 |
| Wash 2 | 4+ | 4+ | 4.0 |
| Wash 3 | 4+ | 4+ | 4.0 |
| Untreated | 0 | 0 | |
| Rating Score | | | 16.0 |
| 5.0% Solution | | | |
| Treated | 4+ | 4+ | 4.0 |
| Wash 1 | 4+ | 4+ | 4.0 |
| Wash 2 | 4+ | 4+ | 4.0 |
| Wash 3 | 4+ | 4+ | 4.0 |
| Untreated | 0 | 0 | |
| Rating Score | | | 16.0 |

TABLE V

| SWATCH | 1 | 2 | Avg. |
|---|---|---|---|
| 1.0 % Solution | | | |
| Treated | 4+ | 4+ | 4.0 |
| Wash 1 | 2+ | 2+ | 2.0 |
| Wash 2 | 2+ | 1+ | 1.5 |
| Wash 3 | 1+ | 1+ | 1.0 |
| Untreated | 0 | 0 | |
| Rating Score | | | 8.5 |
| 3.0% Solution | | | |
| Treated | 4+ | 4+ | 4.0 |
| Wash 1 | 3+ | 3+ | 3.0 |
| Wash 2 | 3+ | 2+ | 2.5 |
| Wash 3 | 2+ | 2+ | 2.0 |
| Untreated | 0 | 0 | |
| Rating Score | | | 11.5 |
| 5.0% Solution | | | |
| Treated | 4+ | 4+ | 4.0 |
| Wash 1 | 4+ | 4+ | 4.0 |
| Wash 2 | 4+ | 4+ | 4.0 |
| Wash 3 | 3+ | 3+ | 3.0 |
| Untreated | 0 | 0 | |
| Rating Score | | | 15.0 |

EXAMPLE 9

The substantivity of the product of Example 1 to fiber material is evaluated by a multiple wash test protocol of the type described in Example 8 wherein two (2) cm square swatches of fiber material are exposed to the test materials by dipping into the test solution and blotting to remove excess moisture. The exposed samples are layed on seeded agar plates and then subject to the various steps described in Example 8. The grading system described in Example 7 is used to record the data.

The fiber material substantivity data are reported in Table VI.

TABLE VI

| SWATCH | 1 | 2 | 3 | 4 | Avg. |
|---|---|---|---|---|---|
| 1.0 % Solution | | | | | |
| Treated | 4+ | 4+ | 4+ | 4+ | 4.0 |
| Wash 1 | 2+ | 3+ | 2+ | 4+ | 2.8 |

TABLE VI-continued

| SWATCH | 1 | 2 | 3 | 4 | Avg. |
|---|---|---|---|---|---|
| Wash 2 | 0.5+ | 1+ | 0 | 1+ | 1.0 |
| Wash 3 | 0 | 0 | 0 | 0 | 0.0 |
| Untreated | 0 | 0 | 0 | 0 | 0.0 |
| | | | | Rating Score | 7.8 |
| *3.0% Solution* | | | | | |
| Treated | 4+ | 4+ | 4+ | 4+ | 4.0 |
| Wash 1 | 3+ | 2+ | 4+ | 3+ | 3.0 |
| Wash 2 | 1+ | 0 | 1+ | 1+ | 0.8 |
| Wash 3 | 0.5+ | 0 | 0 | 0 | 0.1 |
| Untreated | 0 | 0 | 0 | 0 | 0.0 |
| | | | | Rating Score | 7.9 |
| *5.0% Solution* | | | | | |
| Treated | 4+ | 4+ | 4+ | 4+ | 4.0 |
| Wash 1 | 3+ | 4+ | 4+ | 4+ | 3.8 |
| Wash 2 | 1+ | 0.5+ | 0.5+ | 2+ | 1.0 |
| Wash 3 | 1+ | 0 | 0 | 0 | 0.3 |
| Untreated | 0 | 0 | 0 | 0 | 0.0 |
| | | | | Rating Score | 9.1 |

EXAMPLE 10

Using in vitro test methodology based on the International Planned Parenthood Federation (IPPF) Agreed Test spermicidal assay as described in Example 6, evidence of inactivation of human sperm by various synthetic phospholipid compounds is evaluated.

The synthetic phospholipid compounds evaluated for spermicidal activity in this example are:

Product A - Cocamidopropyl PG-Dimonium Chloride Phosphate available commercially under the tradename PHOSPHOLIPID PTC from Mona Industries.

Product B - Stearamidopropyl PG-Dimonium Chloride Phosphate available commercially under the tradename PHOSPHOLIPID SV from Mona Industries.

Product A and Product B are screened for spermicidal activity in 1.0%, 3.0% and 5.0% aqueous solutions.

The 3.0% and 5.0% solutions of Product A and Product B meet the requirements of the IPPF Agreed Test by inactivation of human sperm from three different individuals after ten (10) second contact time.

EXAMPLE 11

The skin substantivity of Product A and Product B of Example 10 is evaluated by the multiple wash test protocol described in Example 7. The degree of residual activity or skin substantivity is determined by clarity of inhibition surrounding the imprints on agar plates seeded with *Staphylococcus epidermidis*. The grading system described in Example 7 is used to record the data.

Skin substantivity data for Product A is reported in Table VII and data for Product B is reported in Table VIII.

TABLE VII

| | PRODUCT A | | |
|---|---|---|---|
| PANALIST | 1 | 2 | Avg. |
| *1.0% Solution* | | | |
| Treated | 3+ | 3+ | 3.0 |
| Wash 1 | 2+ | 2+ | 2.0 |
| Wash 2 | 2+ | 2+ | 2.0 |
| Wash 3 | 0+ | 0+ | 0.0 |
| Untreated | ½+ | ½+ | 0.5 |
| | | Rating Score | 7.5 |
| *3.0% Solution* | | | |
| Treated | 3+ | 3+ | 3.0 |
| Wash 1 | 3+ | 3+ | 3.0 |
| Wash 2 | 2+ | 2+ | 2.0 |
| Wash 3 | 1+ | 0+ | 0.5 |

TABLE VII-continued

| | PRODUCT A | | |
|---|---|---|---|
| PANALIST | 1 | 2 | Avg. |
| Untreated | ½+ | ½+ | |
| | | Rating Score | 8.5 |
| *5.0% Solution* | | | |
| Treated | 4+ | 4+ | 4.0 |
| Wash 1 | 3+ | 3+ | 3.0 |
| Wash 2 | 3+ | 2+ | 2.5 |
| Wash 3 | 1+ | ½+ | .75 |
| Untreated | ½+ | ½+ | |
| | | Rating Score | 10.25 |

TABLE VIII

| | PRODUCT B | | |
|---|---|---|---|
| PANALIST | 1 | 2 | Avg. |
| *3.0% Solution* | | | |
| Treated | 3+ | 4+ | 3.5 |
| Wash 1 | 3+ | 3+ | 3.0 |
| Wash 2 | 2+ | 2+ | 2.0 |
| Wash 3 | ½+ | 1+ | .75 |
| Untreated | ½+ | ½+ | |
| | | Rating Score | 9.25 |
| *5.0% Solution* | | | |
| Treated | 4+ | 4+ | 4.0 |
| Wash 1 | 3+ | 3+ | 3.0 |
| Wash 2 | 2+ | 3+ | 2.5 |
| Wash 3 | 1+ | 1+ | 1.0 |
| Untreated | ½+ | ½+ | |
| | | Rating Score | 10.5 |

EXAMPLE 12

The substantivity of Product A and Product B of Example 10 to lambskin and latex-type condoms is evaluated by a multiple wash test protocol of the type described in Example 8.

Lambskin condom substantivity data for Product A are reported in Table IX and for Product B are reported in Table X. Latex condom substantivity data for Product A are reported in Table XI and for Product B are reported in Table XII.

TABLE IX

| | PRODUCT A - LAMBSKIN | | |
|---|---|---|---|
| SWATCH | 1 | 2 | Avg. |
| *3.0% Solution* | | | |
| Treated | 4+ | 4+ | 4.0 |
| Wash 1 | 3+ | 3+ | 3.0 |
| Wash 2 | 2+ | 2+ | 2.0 |
| Wash 3 | 2+ | 1+ | 1.5 |
| Untreated | 0 | 0 | |
| | | Rating Score | 10.5 |
| *5.0% Solution* | | | |
| Treated | 4+ | 4+ | 4.0 |
| Wash 1 | 4+ | 4+ | 4.0 |
| Wash 2 | 4+ | 4+ | 4.0 |
| Wash 3 | 3+ | 3+ | 3.0 |
| Untreated | 0+ | 0+ | |
| | | Rating Score | 15.0 |

TABLE X

| | PRODUCT B - LAMBSKIN | | |
|---|---|---|---|
| SWATCH | 1 | 2 | Avg. |
| *3.0% Solution* | | | |
| Treated | 4+ | 4+ | 4.0 |
| Wash 1 | 2+ | 3+ | 2.5 |
| Wash 2 | 2+ | 2+ | 2.0 |
| Wash 3 | ½+ | ½+ | 0.5 |
| Untreated | 0+ | 0 | |
| | | Rating Score | 9.0 |

TABLE X-continued

| PRODUCT B - LAMBSKIN | | | |
|---|---|---|---|
| SWATCH | 1 | 2 | Avg. |
| *5.0% Solution* | | | |
| Treated | 4+ | 4+ | 4.0 |
| Wash 1 | 4+ | 4+ | 4.0 |
| Wash 2 | 3+ | 3+ | 3.0 |
| Wash 3 | 2+ | 2+ | 2.0 |
| Untreated | 0+ | 0+ | |
| | | Rating Score | 13.0 |

TABLE XI

| PRODUCT A - LATEX | | | |
|---|---|---|---|
| SWATCH | 1 | 2 | Avg. |
| *3.0% Solution* | | | |
| Treated | 4+ | 4+ | 4.0 |
| Wash 1 | 3+ | 2+ | 2.5 |
| Wash 2 | 2+ | 1+ | 2.0 |
| Wash 3 | ½+ | ½+ | 0.5 |
| Untreated | ½+ | ½+ | |
| | | Rating Score | 9.0 |
| *5.0% Solution* | | | |
| Treated | 4+ | 4+ | 4.0 |
| Wash 1 | 4+ | 4+ | 4.0 |
| Wash 2 | 3+ | 3+ | 3.0 |
| Wash 3 | 2+ | 2+ | 2.0 |
| Untreated | 0+ | 0+ | |
| | | Rating Score | 13.0 |

TABLE XII

| PRODUCT B - LATEX | | | |
|---|---|---|---|
| SWATCH | 1 | 2 | Avg. |
| *3.0% Solution* | | | |
| Treated | 4+ | 4+ | 4.0 |
| Wash 1 | 4+ | 4+ | 4.0 |
| Wash 2 | 4+ | 4+ | 4.0 |
| Wash 3 | 3+ | 3+ | 3.0 |
| Untreated | ½+ | ½+ | |
| | | Rating Score | 15.0 |
| *5.0% Solution* | | | |
| Treated | 4+ | 4+ | 4.0 |
| Wash 1 | 4+ | 4+ | 4.0 |
| Wash 2 | 4+ | 4+ | 4.0 |
| Wash 3 | 4+ | 4+ | 4.0 |
| Untreated | ½+ | ½+ | |
| | | Rating Score | 16.0 |

Having now fully described the invention, it will be apparent to one of ordinary skill in the art that many changes and modifications can be made thereto without departing from the spirit or scope of invention as set forth herein.

What is claimed is:

1. A method of providing spermicidal activity to a substrate subject to contact by human and animal sperm which comprises treating a substrate subject to contact by human and animal sperm with a spermicidally effective amount of a spermicidal agent selected from a synthetic phospholipid of the formula:

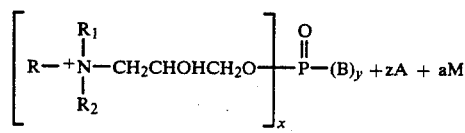

wherein:
x=1
x+y=3;
z=x;
a=0 to 2;
B=O⁻ or OM;
A=Anron;
M is a cation;
R, R₁ and R₂ are the same or different and are alkyl, hydroxyalkyl, alkyl aryl or alkenyl groups of up to 16 carbon atoms with the proviso that the total carbon atoms n R+R₁+R₂ is between 10 and 24, and

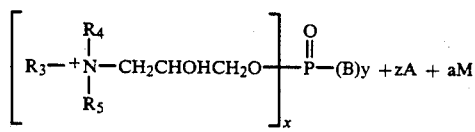

wherein:
x is as hereinabove defined;
x+y=3;
z=x;
a=0 to 2;
B=O⁻ or OM;
A is Anion;
M is a Cation;
R₃ is an amidoamine moiety of the formula:

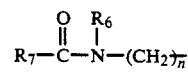

wherein:
R₇ is alkyl, alkenyl, alkoxy or hydroxyalkyl of from 5 to 21 carbon atoms each, or aryl or alkaryl of up to 20 carbon atoms;
R₆ is hydrogen or alkyl, hydroxyalkyl or alkenyl of up to 6 carbon atoms each or cycloalkyl of up to 6 carbon atoms, polyoxyalkylene of up to 10 carbon atoms;
R₄ and R₅, which may be the same or different, are selected from alkyl, hydroxyalkyl, carboxyalkyl of up to 6 carbon atoms in each alkyl moiety, and polyoxyalkylene of up to 10 carbon atoms, in addition R₄ and R₅ taken together with the nitrogen to which they are attached may represent an N-heterocycle; and
n is an integer from about 2 to 6;
or mixtures thereof.

2. The method of providing spermicidal activity according to claim 1, wherein the spermicidal agent is a synthetic phospholipid of the formula:

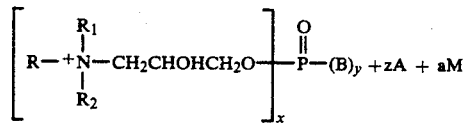

wherein:
x=1 to 3 or mixtures thereof;
x+y=3;
z=x;
a=0 to 2;
B=O⁻ or OM;
A=Anion;
M is a cation;

R, $R_1$ and $R_2$ are the same or different and are alkyl, hydroxyalkyl, alkyl aryl or alkenyl groups of up to 16 carbon atoms with the proviso that the total carbon atoms in $R+R_1+R_2$ is between 10 and 24.

3. A method of providing spermicidal activity to a substrate subject to contact by human and animal sperm which comprises treating a substrate subject to contact by human and animal sperm with a spermicidally effective amount of a spermicidal agent comprising a synthetic phospholipid of the formula:

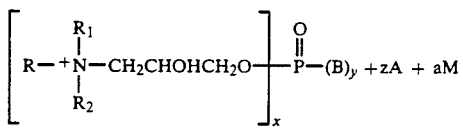

wherein:
$x = 1$ to 3 or mixtures thereof;
$x+y=3$;
$z=x$;
$a=0$ to 2;
$B=O^-$ or OM;
$A=$ Anion;
R, $R_1$ and $R_2$ are the same or different and are alkyl, hydroxyalkyl, alkyl aryl or alkenyl groups of up to 16 carbon atoms with the proviso that the total carbon atoms in $R+R_1+R_2$ is between 10 and 24:

* * * * *